(12) United States Patent
Peter et al.

(10) Patent No.: US 10,393,764 B2
(45) Date of Patent: Aug. 27, 2019

(54) SOLID WASTE REMOVAL

(71) Applicant: Roche Molecular Systems, Inc., Pleasanton, CA (US)

(72) Inventors: Andre Peter, Meggen (CH); Markus Troxler, Rotkreuz (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 109 days.

(21) Appl. No.: 15/184,043

(22) Filed: Jun. 16, 2016

(65) Prior Publication Data

US 2016/0370395 A1    Dec. 22, 2016

(30) Foreign Application Priority Data

Jun. 19, 2015 (EP) .................................. 15172874

(51) Int. Cl.
*G01N 35/04* (2006.01)
*G01N 35/00* (2006.01)
(Continued)

(52) U.S. Cl.
CPC ....... *G01N 35/00722* (2013.01); *G01N 35/00* (2013.01); *G01N 35/00663* (2013.01);
(Continued)

(58) Field of Classification Search
CPC ................. G01N 35/04; G01N 35/02; G01N 2035/0465; G01N 2035/0491;
(Continued)

(56) References Cited

U.S. PATENT DOCUMENTS 3,802,782 A    4/1974 Natelson
4,985,207 A *  1/1991 Hayashi ................ G01N 35/04
                                          422/552
(Continued)

FOREIGN PATENT DOCUMENTS

CA    1313113 C     1/1993
CN    1875278      12/2006
(Continued)

OTHER PUBLICATIONS

European Search Report for EP 15 17 2874, https://register.epo.org/application?number=EP15172874&lng=en&tab=doclist, dated Nov. 25, 2015, obtained by Examiner on Sep. 6, 2018, 2 pages. (Year: 2015).*
(Continued)

*Primary Examiner* — Christine T Mui
(74) *Attorney, Agent, or Firm* — Pamela C. Ancona (57) ABSTRACT

Disclosed herein is a method for depositing solid waste into a waste bin in an automated analyzer having a transport mechanism for transporting solid waste to a waste bin. The method includes providing a transport mechanism including a sliding mechanism, a parking position, and an opening that is proximal to the waste bin. The sliding mechanism includes a slider and an extendable ramp and the slider pushes the solid waste along the ramp into the waste bin. The method also includes placing solid waste into the parking position, contacting the solid waste with the slider, and pushing said solid waste towards the waste bin along the ramp until the solid waste moves along the extendable ramp into the waste bin.

3 Claims, 6 Drawing Sheets

(51) Int. Cl.
  *G01N 35/02* (2006.01)
  *G01N 35/10* (2006.01)

(52) U.S. Cl.
  CPC ............. *G01N 35/04* (2013.01); *G01N 35/10* (2013.01); *G01N 2035/00277* (2013.01); *G01N 2035/00891* (2013.01)

(58) Field of Classification Search
  CPC ... G01N 2035/0401; G01N 2035/0439; G01N 2035/0474; G01N 35/00722; G01N 35/00584
  USPC .............................................. 436/48, 47, 43
  See application file for complete search history.

(56) References Cited

U.S. PATENT DOCUMENTS

| | | | |
|---|---|---|---|
| 5,242,659 A | | 9/1993 | Wurschum |
| 5,359,907 A | * | 11/1994 | Baker ................ G01N 15/0205 356/335 |
| 5,746,299 A | * | 5/1998 | Molbak .................... G07D 3/14 194/200 |
| 5,858,732 A | | 1/1999 | Solomon et al. |
| 6,284,459 B1 | * | 9/2001 | Nova .................... B01J 19/0046 422/68.1 |
| 6,284,469 B1 | | 9/2001 | Hope et al. |
| 9,879,328 B2 | | 1/2018 | Rey et al. |
| 9,909,169 B2 | | 3/2018 | Will |
| 9,914,970 B2 | | 3/2018 | Ladner et al. |
| 9,914,975 B2 | | 3/2018 | Meldgaard et al. |
| 2005/0150314 A1 | | 7/2005 | Staples et al. |
| 2008/0175756 A1 | | 7/2008 | Justin et al. |
| 2010/0126286 A1 | | 5/2010 | Self et al. |
| 2012/0058900 A1 | | 3/2012 | Gisler et al. |
| 2013/0065797 A1 | | 3/2013 | Silbert et al. |
| 2014/0295563 A1 | * | 10/2014 | Matsuura ............... G01N 35/04 436/48 |

FOREIGN PATENT DOCUMENTS

| | | | |
|---|---|---|---|
| CN | 104297502 | 1/2015 | |
| DE | 102012206239 A1 | 10/2013 | |
| JP | 2221866 A | 9/1990 | |
| JP | 2001507118 A | 5/2001 | |
| JP | 2007017211 A | 1/2007 | |
| JP | 2013-069967 | * 3/2013 | ............. G01N 35/00 |
| JP | 5450465 B2 | 3/2014 | |
| WO | 2010144859 A2 | 12/2010 | |

OTHER PUBLICATIONS

European Search Opinion for EP 15 17 2874, https://register.epo.org/application?number=EP15172874&lng=en&tab=doclist, dated Nov. 25, 2015, obtained by Examiner on Sep. 6, 2018, 4 pages. (Year: 2015).*

* cited by examiner

SOLID WASTE REMOVAL

FIELD OF THE INVENTION

The present invention relates to removal of used solid waste within an automated analyzer.

BACKGROUND OF THE INVENTION

Automated analyzers use different types of consumables, e.g. multiwell plates, tip racks, reagent cassettes, and/or other types of solid containers to perform an automated analytical assay. Once the assay steps for which a consumable or container is needed has been performed and the consumable or container is no longer needed, it is commonly transported to a waste compartment or waste bin as solid waste. The solid waste is accumulated in the waste compartment or waste bin. When the compartment or waste bin is full, the operator has to empty the compartment or remove the waste bin and either replace it with an empty waste bin or empty the waste bin and place it back in the analyzer. The waste capacity often dictates the maximum number of tests the analyzer can perform before the waste is removed.

In US20130065797, the filling level of a waste bin is monitored using a camera. The solid waste bin can be opened each time the waste bin drawer is emptied.

The present invention provides for a new method, analyzer and system which improve the waste capacity of an automated analyzer.

SUMMARY OF THE INVENTION

The present invention relates to a method for dropping solid waste into a waste bin in an automated analyzer. The method comprises providing a transport mechanism for transporting said solid waste to said waste bin. The transport mechanism comprises a sliding mechanism with a slider, said slider being configured to push the solid waste into the waste bin. The sliding mechanism further comprises at its end a ramp, wherein said ramp is extendable over and into the waste bin and at least partly flexible. The method further comprises placing a solid waste into a parking position associated with the transport mechanism, wherein said parking position is located between the slider and an opening of the transport mechanism, said opening of the transport mechanism being in proximity to the waste bin. Further, the method comprises pushing said solid waste towards the waste bin along the extendable ramp with said slider until said solid waste glides on the extendable ramp into the waste bin.

The present invention also relates to an automated analyzer comprising a waste bin, said waste bin being configured to receive solid waste, wherein said analyzer comprises a transport mechanism for transporting said solid waste to said waste bin, said transport mechanism comprising a sliding mechanism with a slider, said slider being configured to push the solid waste into the waste bin, said sliding mechanism further comprising at its end a ramp, wherein said ramp is extendable over and into the waste bin and at least partly flexible.

The present invention also relates to a system comprising an automated analyzer as described herein and a computer controller. The computer controller is configured to push solid waste into the waste bin and to sense if a solid waste is present on top of a pile and to push said solid waste into another location of the waste bin. The computer controller is further configured to issue a warning message to a screen when solid waste on top of a pile cannot be moved to a different location within the waste bin.

DETAILED DESCRIPTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The present invention relates to a method for dropping solid waste into a waste bin in an automated analyzer. The method comprises providing a transport mechanism for transporting said solid waste to said waste bin. The transport mechanism comprises a sliding mechanism with a slider, said slider being configured to push the solid waste into the waste bin. The sliding mechanism further comprises at its end a ramp, wherein said ramp is extendable over and into the waste bin and at least partly flexible. The method further comprises placing a solid waste into a parking position associated with the transport mechanism, wherein said parking position is located between the slider and an opening of the transport mechanism, said opening of the transport mechanism being in proximity to the waste bin. Further, the method comprises pushing said solid waste towards the waste bin along the extendable ramp with said slider until said solid waste glides on the extendable ramp into the waste bin.

In one embodiment, the ramp is extendable along a bent curve over and into the waste bin and the ramp is at least partly made of a flexible material.

The term "solid waste" relates to solid parts used in an analytical system or apparatus which, after use, have to be removed from the automated analyzer. In one specific embodiment, solid waste comprises consumables. It is understood that the term "consumables" as used herein only refers to solid consumables and not to other types of matter used in an analytical device, such as reagents. Such consumables may include, without limitation, pipette tip racks comprising used pipette tips, used single tubes, used multiwell plates, used reagent cassettes etc. While some consumables may be used only once in the automated analyzer and then have to be removed, others may be used multiple times before they are used up and have to be removed from the automated analyzer. Removal of such solid waste is effected by dropping the solid waste in a waste bin.

The term "automated analyzer" as used herein refers to any kind of automated or semi-automated device for use in laboratory work in the clinical, chemical, biological, immunology or pharmaceutical area or the like. Such a laboratory device may comprise, amongst other things, at least one of an analytical instrument (such as clinical chemistry analyzers, coagulation chemistry analyzers, immunochemistry analyzers, urine analyzers), a transfer device (such as a conveyor, gripper, magnetic transfer surface), a storage unit, a liquid processing unit (such as a pipetting unit), a processor (such as a sample preparation device), a user interface, a mixing unit (such as a stirrer; a shaker or an agitator), a tempering device (such as a heater/cooler), a waste station, an aliquoter, a data management system, laboratory information system (LIS) or the like.

The term "transport mechanism" as used herein relates to any transport mechanism that is suitable to transport a solid waste into a waste bin. The transport mechanism comprises a sliding mechanism with a slider. The transport mechanism may also comprise other transport devices, such as grippers or conveyors, to transport the solid waste from the location of its last use to the sliding mechanism.

The term "sliding mechanism" as used herein relates to a mechanism which comprises a slider. The sliding mechanism allows the solid waste to slide into the waste bin. The sliding mechanism further comprises at its end a ramp. The ramp is extendable over and into the waste bin and at least partly flexible. Thus, when a solid waste is pushed onto the ramp, the ramp bends downwards and allows the solid waste to glide into the waste been located underneath the ramp.

The term "slider" relates to a device which is configured to push the solid waste in the direction of the waste bin.

The term "ramp" as used herein relates to the end part of the sliding mechanism. The ramp is partly flexible. When a solid waste, such as a tip rack or a multiwell plate, is pushed onto the ramp by the slider, the ramp bends downwards and allows the solid waste to glide into the waste bin located underneath the ramp.

The term "extendable" as used herein means that the ramp is capable to extend over and into the waste bin. Thus, the ramp does not have to be permanently in such an extended position. It may move between a position where it does not extend over and into the waste bin and a position which extends over and into the waste bin. Such a position may be taken when either no solid waste needs to be dropped into the waste bin, or when the waste bin has to be removed for emptying. When a solid waste has to be dropped into the waste bin and is pushed onto the ramp, the ramp may then move from the position where it does not extend over and into the waste bin to the position which extends over and into the waste bin. In this position, the ramp, then, bends downwards and allows the solid waste to glide into the waste bin. The ramp may also take the position which extends over and into the waste bin to detect if the waste bin is filled or if there is still space in the waste bin for further solid waste. Thus, in one embodiment, when the ramp is extended over the bin, the partly flexible ramp is sliding along a bent curve, allowing the ramp to move over and into the waste bin without contacting the waste bin. As the consumable is pushed onto the ramp, the ramp moves forward and bends, allowing the consumable to glide into the waste bin.

The term "at least partly flexible" as used herein relates to a property of the ramp. The property is due to the material of the ramp. Any material that allows the ramp to extend over and into the waste bin from a position over the waste bin, even if no solid waste is located on the ramp, is suitable. Such materials may include thermoplastic materials, and as specific non-limiting examples, Polyoxymethylene (POM) or Polyethylene (PE).

The term "parking position" as used herein relates to a position associated with the transport mechanism. The parking position is on the side of the slider which is proximal to the waste bin. The solid waste to be transported to the waste bin is placed on the parking position.

The term "opening" as used herein relates to an opening in the transport mechanism on the side where the waste bin is located that allows the solid waste to be pushed to the ramp, to move through this opening and to glide over the ramp into the waste bin.

The term "proximity" as used herein relates to the location of the opening in the transport mechanism. The transport mechanism has to be open on the side which is in proximity to the waste bin such that the ramp is capable to extend over and into the waste bin and the solid waste can glide down the ramp into the waste bin.

The term "glide" as used herein relates to the movement of the solid waste when it moves over the ramp. When the solid waste reaches the end of the ramp, it will drop into the waste bin.

The advantage of such a method of dropping, solid waste into a waste bin in an automated analyzer is that solid waste can be distributed better in the waste bin. This increases the capacity of the waste bin. The more solid waste the waste bin can take up, the longer it takes until it has to be removed and emptied. This significantly influences the walk-away time for the automated analyzer. If the analyzer is set to run continuously, the walkaway time is governed by the time it takes to use the unused consumables loaded on the automated analyzer, or the time it takes for the waste bin to be full, or the time until reagents are used up. If the automated analyzer is designed to take up a sufficient amount of new, unused consumables and reagents, then, a premature requirement to empty the waste bin due to inefficient filling of the waste bin can significantly impair the maximum walk-away time as originally designed by the capacity to load empty consumables and reagents. This can be avoided with the automated analyzer according to the present invention. Another advantage is that the extendable ramp of the present invention is integrated into a sliding mechanism and thereby ensures that the solid waste is pushed into the waste bin.

In one embodiment, a solid waste is loaded into the parking position. The slider is positioned on the side of the solid waste which opposes the side proximal to the opening. In one specific embodiment, the slider is attached to a conveyor belt and executes a horizontal movement toward a defined end position. Thus, the slider is moved by the conveyor belt. In a more specific embodiment, the end position is close to or at the opening of the transport mechanism.

In one embodiment, the ramp is coupled to the conveyor belt. In a specific embodiment, the movement of the ramp is synchronous to the movement of the slider. In a more specific embodiment, the ramp is moving along a bent curve, allowing the shaft to move into the waste bin located underneath the extended ramp.

In one specific embodiment, the waste bin is located in a waste drawer. The operator can open the waste drawer to add or remove the waste bin. As the ramp of the present invention moves into and out of the waste bin in a contactless manner, no additional weight occurs for the waste drawer. This makes it easier to open and close the waste drawer, and reduces wear of the waste drawer. The term "contactless" as used herein is understood to mean that the extendable ramp moves into and out of the waste bin without contacting the waste bin.

In one specific embodiment, the solid waste container of the method described herein comprises a solid waste bag. In one embodiment, it comprises more than one solid waste bag. A further advantage is that the present invention reduces the kinetic and potential energy of solid waste which leads to a reduced stress of the solid waste bags and, hence, less perforation of the solid waste bags occurs. Furthermore, the ramp described herein guides consumables holding pipette tips, such as tip racks, into the waste bin which leads to significantly less tips dropping out of the containers and consequently, lower requirements for solid waste has regarding perforation resistance.

In one embodiment, said extendable ramp is configured as a tactile sensor for detecting jammed solid waste along a sliding path.

The term "tactile sensor" as used herein relates to the ability of the ramp to sense a solid item by touching it. Thus, the ramp can detect the fill level of the waste bin by sensing whether it touches something solid (i.e. a solid waste) or not. If it touches a solid waste, this means that the waste bin has a certain fill level. If it does not touch anything solid, this means that there is still enough space in the waste bin for further solid waste. The tactile sensor also allows to detect jammed solid waste.

The term "jammed solid waste" as used herein relates to solid waste, e.g. in specific embodiments consumables, which have become stuck in the waste bin and prevent the waste bin from taking up more solid waste although there would still be space in it. In one embodiment, jammed solid waste may be the result of random piles being formed by dropped solid waste. E.g. tip racks may form piles when dropping in the waste bin. Such piles may build up until the top end of the waste bin is reached. The waste bin then cannot take up more solid waste since the transport mechanism would be blocked and additional solid waste would be prevented from gliding into the waste bin.

The term "sliding path" as used herein relates to the path that a solid waste takes when being transported into the waste bin. The sliding path, thus, describes the path of the sliding mechanism.

The term "detecting jammed solid waste" as used herein is understood to mean that when the ramp touches jammed solid waste, this is translated into a signal which is provided to the automated analyzer.

In a specific embodiment, said extendable ramp is configured to move solid waste present on top of a pile inside the waste bin to another location inside the waste bin. This leads to a better distribution of the solid waste.

As mentioned hereinbefore, it was observed that solid waste can build up piles in a waste bin. Such buildups are also referred to as jammed solid waste. The solid waste present on top of the piles can be moved by the extendable ramp. When it is moved, it is moved to another, still empty location of the waste bin. This results in a better distribution of the solid waste in the waste bin. More solid waste can be filled into the waste bin until the solid waste in the bin reaches the upper end of the waste bin, and the waste bin has to be removed, by the operator and emptied.

In one specific embodiment, the extendable ramp is configured to detect jammed solid waste. In a more specific embodiment, the extendable ramp is configured to detect jammed solid waste which cannot be moved to a different location within the waste bin. This permits a better distribution of the solid waste in the waste bin.

In an even, more specific embodiment, the automated analyzer additionally comprises a sensor system functionally coupled to said ramp and configured to monitor the level of piled solid waste inside the waste bin.

The extendable ramp is able to detect the level of solid waste more reliably than an optical sensor. This is due to the ramp sliding along the dropping zone of the solid waste, hence any piled solid waste will be detected.

In one embodiment, the sensor system for detecting the level of solid waste in the waste bin comprises detection of motor current of the ramp drive.

In a further specific embodiment, said automated analyzer comprises a computer controller and a screen, wherein said computer controller is configured to issue a warning message when solid waste on top of a pile cannot be moved to a different location within the waste bin.

The term "a computer controller" as used herein relates to a computer controller associated with the automated analyzer or the system comprising the automated analyzer.

The term "a warning message" as used herein relates to a message displayed by the computer controller on a screen, or an indicator (e.g. a light or a visual message or a voice message) being activated to warn the operator that the waste bin has to be emptied.

In one embodiment, the warning message is displayed on a screen. The term "a screen" as used herein relates to a screen mounted on the automated analyzer. Such screens are well known in the art and may display different types of information relating to the analyzer status.

In one embodiment, a movable lid is attached to the conveyor belt and opens or closes the parking position, depending on the position of the slider.

The present invention also relates to an automated analyzer comprising a waste bin, said waste bin being configured to receive solid waste. The analyzer comprises a transport mechanism for transporting the solid waste to the waste bin. The transport mechanism comprises a sliding mechanism with a slider. The slider is configured to push the solid waste into the waste bin. The sliding mechanism further comprises at its end a ramp, wherein said ramp is extendable over and into the waste bin and at least partly flexible.

The advantage of such an automated analyzer is that solid waste can be distributed better in the waste bin. This increases the capacity of the waste bin. The more solid waste the waste bin can take up, the longer it takes until it has to be removed and emptied. This significantly influences the walk-away time for the automated analyzer. If the analyzer is set to run continuously, the walkaway time is governed by the time it takes to use the unused consumables loaded on the automated analyzer, or the time it takes for the waste bin to be full, or the time until reagents are used up. If the automated analyzer is designed to take up a sufficient amount of new, unused consumables and reagents, then, a premature requirement to empty the waste bin due to inefficient filling of the waste bin can significantly impair the maximum walk-away time as originally designed by the capacity to load empty consumables and reagents. This can be avoided with the automated analyzer according to the present invention.

In one specific embodiment, the solid waste container comprises at least one solid waste bag. A further advantage is that the present invention reduces the kinetic and potential energy of solid waste which leads to a reduced stress of the solid waste bags and, hence, less perforation of the solid waste bags occurs. Furthermore, the ramp described herein guides consumables holding pipette tips, such as tip racks, into the waste bin which leads to significantly less tips dropping out of the containers and, consequently, lower requirements for waste bags regarding perforation resistance.

In one specific embodiment, the waste bin is located in a waste drawer. The operator can open the waste drawer to add or remove the waste bin. As the ramp of the present invention moves into and out of the waste bin in a contactless manner, no additional weight occurs for the waste drawer. This makes it easier to open and close the waste drawer, and reduces wear of the waste drawer. The term "contactless" as used herein is understood to mean that the extendable ramp moves into and out of the waste bin without contacting the waste bin.

In one embodiment, said extendable ramp is configured as a tactile sensor for detecting jammed solid waste along a sliding path.

In one specific embodiment, the automated analyzer additionally comprises a sensor system functionally coupled to said ramp and configured to monitor the level of piled solid waste inside the waste bin.

The extendable ramp is able to detect the level of solid waste more reliably than an optical sensor. This is due to the ramp sliding along the dropping zone of the solid waste, hence any piled solid waste will be detected.

In one embodiment, the sensor system for detecting the level of solid waste in the waste bin comprises detection of motor current of the ramp drive.

In a specific embodiment, said extendable ramp is configured to move solid waste present on top of a pile inside the waste bin to another location inside the waste bin. This leads to a better distribution of the solid waste.

As mentioned hereinbefore, it was observed that solid waste can build up piles in a waste bin. Such buildups are also referred to as jammed solid waste. The solid waste present on top of the pile can be moved by the extendable ramp. When it is moved, it is moved to another, still empty location of the waste bin. This results in a better distribution of the solid waste in the waste bin. More solid waste can be filled into the waste bin until the solid waste in the bin reaches the upper end of the waste bin, and the waste bin has to be removed by the operator and emptied.

In one specific embodiment, the extendable ramp is configured to detect jammed solid waste. In a more specific embodiment, the extendable ramp is configured to detect jammed solid waste which cannot be moved to a different location within the waste bin. This permits a better distribution of the solid waste in the waste bin.

In one embodiment, said solid waste comprises consumables. In a specific embodiment, the consumables comprise at least one of a tip rack, a multiwell plate, a reagent container.

In one embodiment, the automated analyzer comprises a movable lid attached to the conveyor belt and configured to open or close the parking position, depending on the position of the slider.

Further embodiments of the automated analyzer of the present invention are as described for the method of the present invention.

The present invention also relates to a system comprising an automated analyzer as described herein and a computer controller. The computer controller is configured to push solid waste into the waste bin and to sense if a solid waste is present on top of a pile and to push said solid waste into another location of the waste bin. The computer controller is further configured to issue a warning message to a screen when solid waste on top of a pile cannot be moved to a different location within the waste bin. Specific embodiments of the automated analyzer or the process controlled by the computer controller are as described for the automated analyzer or the process of the present invention.

An exemplary method for removing solid waste from an automated analyzer comprising the method of the present invention is described hereinafter.

Consumables such as multiwell plates, deep well plates, tip racks are held in the automated analyzer during their use. Once the consumables are ready to waste, a command is given to initiate a waste procedure for the foreseen consumable.

A transport system, such as a conveyor or a gripper transports the consumable to the parking position of the transport mechanism for transporting said solid waste to a waste bin. A sensor detects the presence of the consumable and initiates a method for dropping solid waste into a waste bin. A slider, which is positioned at the side of the consumable which is opposite of the opening of the transport mechanism towards the waste bin, and is attached to a conveyor, executes a horizontal motion towards a defined end position. An extendable and partly flexible ramp which is coupled to the conveyor at the end of the conveyor proximal to the opening of the transport mechanism moves synchronously to the slider as the consumable is being pushed by the slider along the conveyor. Underneath the end position of the slider, a solid waste bin is located. The partly flexible ramp is sliding along a bent curve, allowing the ramp to move over and into the waste bin without contacting the waste bin. As the consumable is pushed onto the ramp, the ramp moves forward and bends, allowing the consumable to glide into the waste bin.

In case the ramp collides with a randomly formed pile of solid waste, a software controlling the movement of the ramp allows detecting and adjusting the force of the ramp to a specific adjusted force. If the ramp collides with a movable consumable, the force will remain below the adjusted force and the ramp will continue its movement, thereby displacing the loose consumable with which it collided. If the ramp collides with a blocked consumable (i.e. when the waste bin is full), the force detected is above the adjusted force. The movement of the ramp is aborted as the consumable cannot be displaced. The control unit with the software controlling the movement of the ramp then registers this as detection of a blocked pile of solid waste. In this manner, the ramp can act as a tactile sensor.

Figure 1:
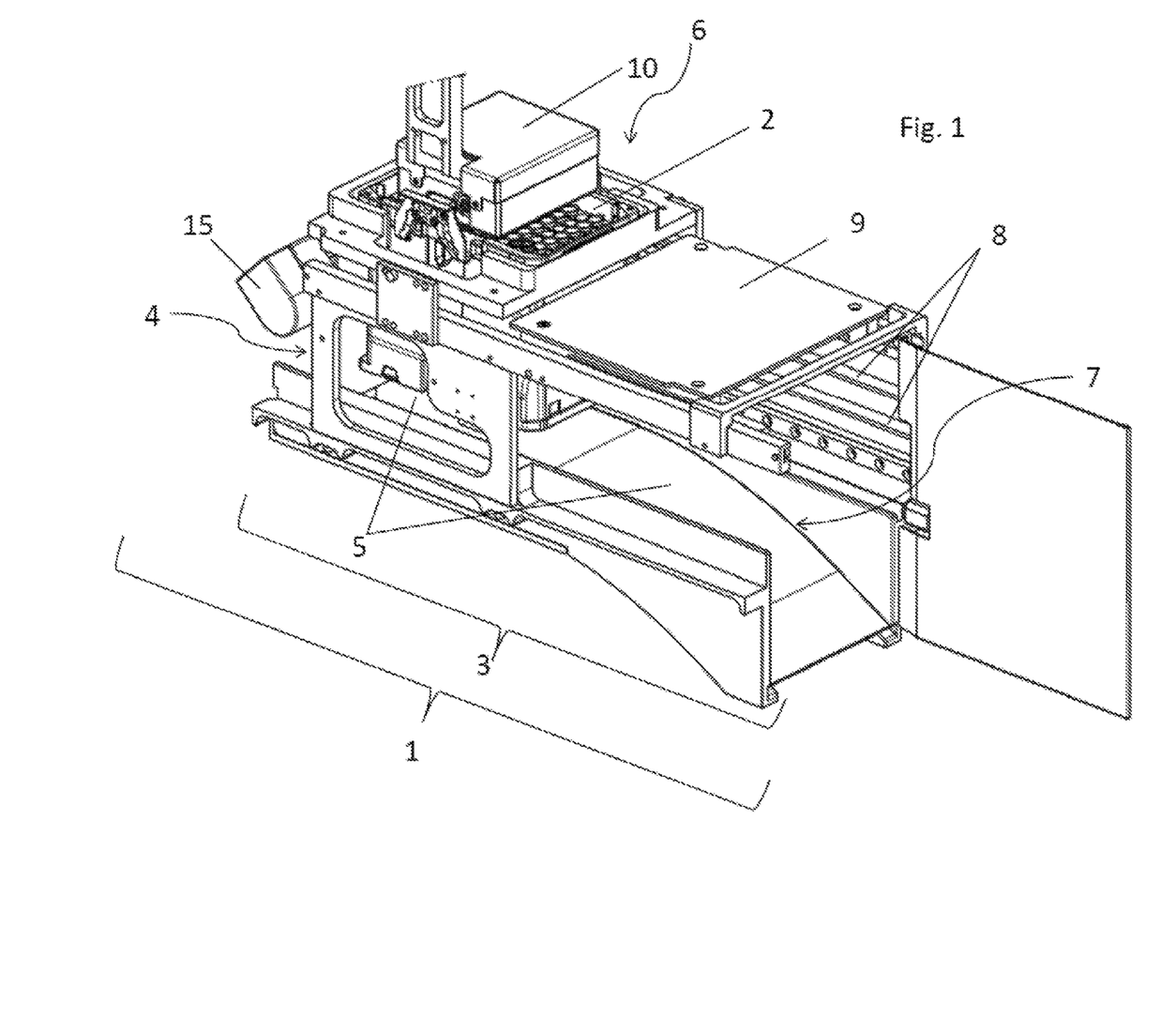
FIG. 1 shows an exemplary transport mechanism for transporting solid waste into a waste bin.

FIG. 1 shows a transport mechanism (1). The transport mechanism (1) comprises a parking position (6). A gripper (10) may load a solid waste (2) in the parking position. Other mechanisms to load a solid waste (2) in a parking position (6) may be envisioned as well, such as, e.g. a conveyor. The conveyor is driven by a motor (15).

The transport mechanism (1) comprises a sliding mechanism (3). The sliding mechanism (3) comprises a slider (4). The slider (4) is located on the distal side, relative to the ramp (5) and the opening (7) of the transport mechanism (1). From this position, the slider (4) may, then, push the solid waste (2) forward onto the extendable ramp (5). In one embodiment, the slider is attached to a conveyor belt (8). The ramp (5), in one embodiment, connected to the conveyor belt (8). In one embodiment, the slider (4) and the extendable ramp (5) are connected to the conveyor belt (8). An opening (7) is present in the transport mechanism (1) on the side of the transport mechanism (1) proximal to the waste bin (12). Furthermore, in one embodiment, the transport mechanism (1) comprises a closure or lid (9). The lid is attached to the conveyor belt. The movement of lid and slider are, thus, synchronized. When the slider moves a solid waste to the bin, the lid moves underneath the parking position. This allows prevention of contamination or prevents aerosol distribution.

Figure 2:
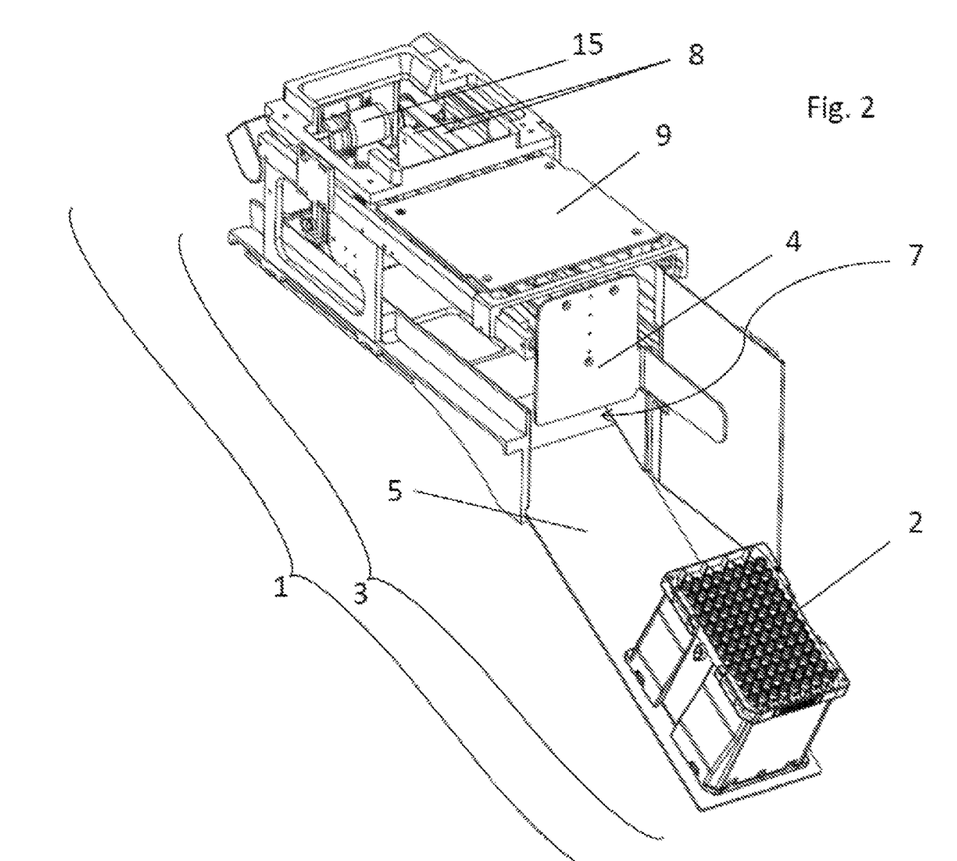
FIG. 2 shows a transport mechanism with the extended ramp.

Once the solid waste (2) is pushed onto the ramp (5), the ramp (5) extends into the waste bin and allows the solid waste (2) to glide into the waste bin. This is shown in FIG. 2. In FIG. 2, it can also be appreciated that the slider (4) has moved to the opening (7) of the transport mechanism (1).

Figure 3A:
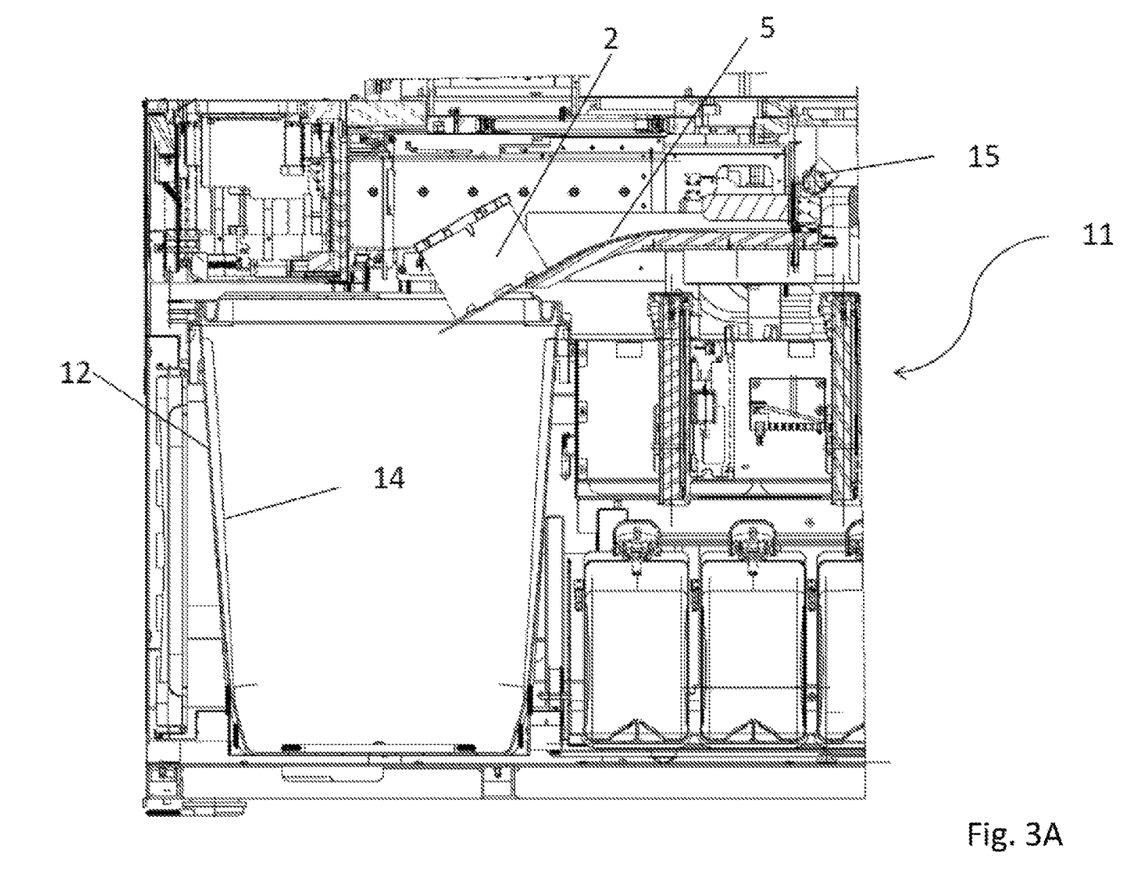
FIGS. 3A, 3B, and 3C show different stages of filling of solid waste in the waste bin.
Figure 3B:
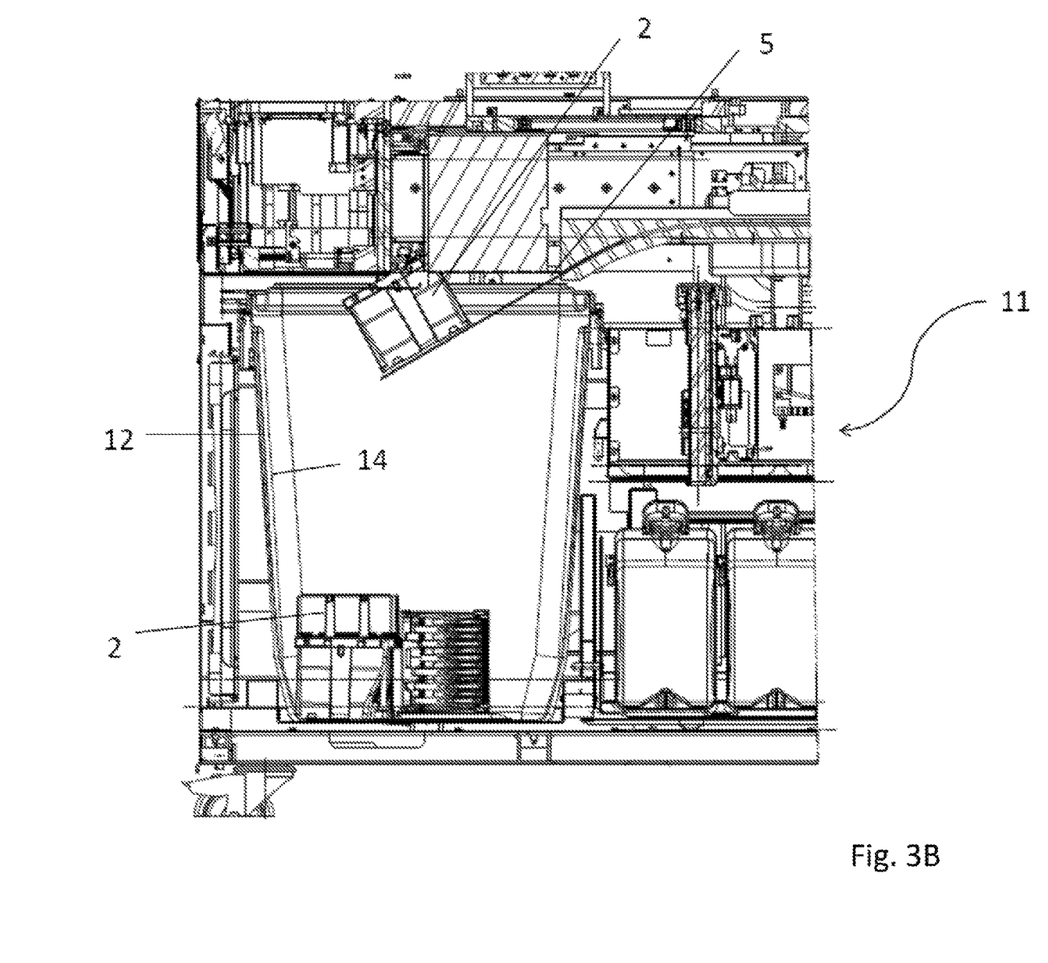
Figure 3C:
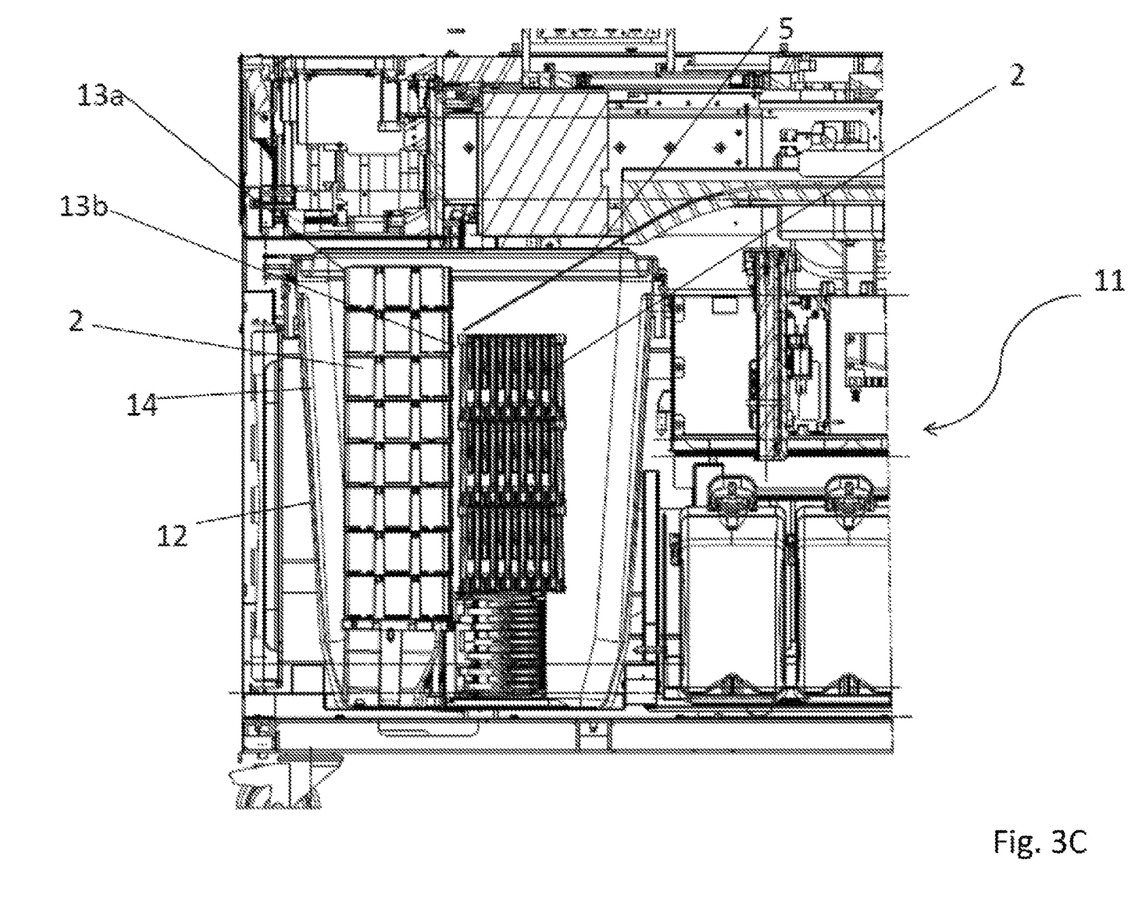

FIG. 3A shows a section of a part of an exemplary automated analyzer (11). Waste bin (12) is shown, and a solid waste (2) sitting on an extendable ramp (5) before gliding into the waste bin (12). A waste bag (14) is placed in waste bin (12). In FIG. 3B, solid waste (2) is already present in the waste bin (12). The extendable ramp (5) is seen in an extended state, extending into the waste bin (12). FIG. 3C shows piles of solid waste (13a) and (13b). The extendable ramp (5) moves until it collides with pile (13a). If pile (13a) is a blocking pile, the control unit controlling the movement of extendable ramp (5) registers that the extendable ramp (5) cannot move beyond the position of pile (13a).

Figure 4A:
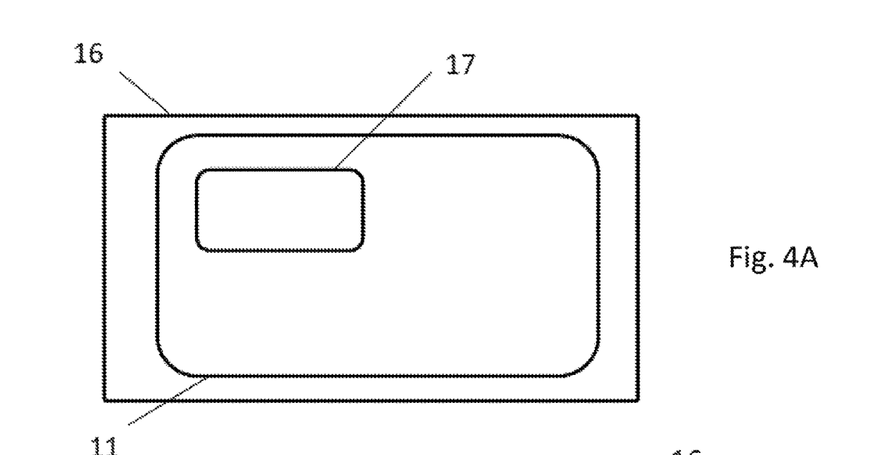
FIGS. 4A and 4B show two embodiments of a system of the present invention.
Figure 4B:
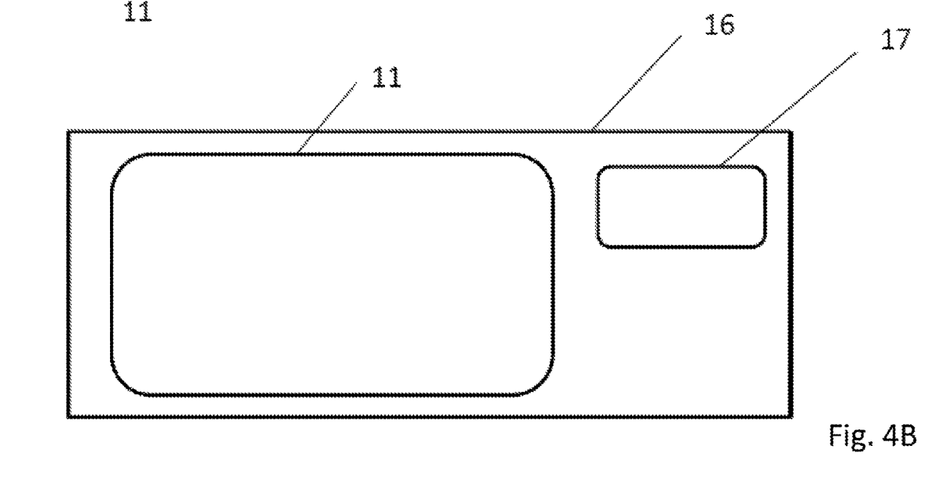

FIGS. 4A and 4B each show a system (16) comprising an analyzer (11) and a computer controller (17). In FIG. 4A, the computer controller (17) is located inside the automated analyzer (11). In FIG. 4B, the computer controller (17) of the system (16) is located outside the automated analyzer (11). In one embodiment, the analyzer (11) is as described herein. As described herein, the computer controller (17) is configured to push solid waste (2) into the waste bin (12) and to sense if a solid waste (2) is present on top of a pile (13) and to push said solid waste (2) into another location of the waste bin (12).

The present application is not to be limited in scope by the specific embodiments described herein. Indeed, various modifications in addition to those described herein will become apparent to those skilled in the art from the foregoing description and accompanying figures. Such modifications are intended to fall within the scope of the claims.

Various publications are cited herein, the disclosures of which are incorporated by reference in their entireties.

The invention claimed is:

1. A method for depositing solid waste into a waste bin in an automated analyzer, said method comprising the steps of:
   providing a device comprising, from a proximate to a distal end, a slider, a parking position, and an opening, wherein the opening is proximal to the waste bin, and the slider is in communication with an extendable ramp and a motor, wherein said ramp is extendable over and into the waste bin and the ramp is at least partly made of a flexible material,
   placing a solid waste into the parking position,
   contacting the solid waste with the slider,
   pushing said solid waste towards the waste bin along the extendable ramp with said slider until said solid waste moves along the extendable ramp toward the waste bin,
   identifying a fill level of the waste bin by detecting a motor current of the motor, and
   (i) adjusting a force of the ramp, as needed, to a specified adjusted force to enable a continual movement of the solid waste along the extendable ramp into the waste bin; or
   (ii) aborting movement of the solid waste along the extendable ramp into the waste bin if the motor current is above the specified adjusted force.

2. The method of claim 1, wherein said method further comprises moving, via the extendable ramp, the solid waste from the top of a pile inside the waste bin to a different location inside the waste bin.

3. The method of claim 1, wherein the method further comprises detecting, using a computer controller located within the automated analyzer, the presence or absence of a blockage within the waste bin and issuing a warning message if said blockage is present.

\* \* \* \* \*